United States Patent
Hill et al.

(10) Patent No.: US 11,141,560 B2
(45) Date of Patent: *Oct. 12, 2021

(54) DEVICES, SYSTEMS AND METHODS FOR INHIBITING OR DISRUPTING PEDIATRIC ANXIETY

(71) Applicant: Calma Co LLC, New Brighton, MN (US)

(72) Inventors: Courtney A. Hill, Arden Hills, MN (US); Christie Traczyk, Savage, MN (US); Adam Choe, Coon Rapids, MN (US)

(73) Assignee: Calma Co LLC, New Brighton, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/875,103

(22) Filed: May 15, 2020

(65) Prior Publication Data

US 2020/0276408 A1 Sep. 3, 2020

Related U.S. Application Data

(63) Continuation of application No. 15/985,776, filed on May 22, 2018, now Pat. No. 10,661,048.

(Continued)

(51) Int. Cl.
*A61M 21/02* (2006.01)
*A61B 5/16* (2006.01)
(Continued)

(52) U.S. Cl.
CPC ............. *A61M 21/02* (2013.01); *A61B 5/165* (2013.01); *A61B 5/369* (2021.01);
(Continued)

(58) Field of Classification Search
CPC .............. A61M 21/02; A61M 21/0094; A61M 2021/0027; A61M 2021/005; A61M 2205/59
(Continued)

(56) References Cited

U.S. PATENT DOCUMENTS 5,044,378 A 9/1991 Toma et al.
10,661,048 B1 * 5/2020 Hill ........................ G16H 50/20
(Continued)

OTHER PUBLICATIONS

"The Hidden Force of Fragrance," Psychology Today (published Nov. 2007, updated Jun. 2016). Retrieved from the Internet: https://www.psychologytoday.com/us/articles/200711/the-hidden-force-fragrance.

(Continued)

*Primary Examiner* — Samuel G Gilbert
(74) *Attorney, Agent, or Firm* — Gregory W. Smock (57) ABSTRACT

Children who experience anxiety associated with novel situations react physically and emotionally in ways that make it challenging for the child, parents, educators, and providers to proceed with the intended goal of that novel situation. Anxiety in children can be reduced by introducing fun or distracting stimuli that act on specific neural pathways. The stimuli introduced can familiarize a child with the environment in which the procedure will take place and the equipment and people which the child will meet. In the healthcare setting, by using consistent stimuli, and by disrupting anxiety at one or more of a series of stages in which anxiety typically occurs, a reduction in needed anesthesia can be achieved, which is healthier for the child and reduces the costs associated with the medical or dental procedure.

20 Claims, 6 Drawing Sheets

Related U.S. Application Data (60) Provisional application No. 62/509,342, filed on May 22, 2017.

(51) Int. Cl.
  *A61B 5/369* (2021.01)
  *A61M 21/00* (2006.01)

(52) U.S. Cl.
  CPC ............... *A61M 2021/005* (2013.01); *A61M 2021/0022* (2013.01); *A61M 2021/0027* (2013.01)

(58) Field of Classification Search
  USPC .............................................. 600/26, 27, 28
  See application file for complete search history.

(56) References Cited

U.S. PATENT DOCUMENTS

| | | |
|---|---|---|
| 2007/0176920 A1 | 8/2007 | Raijmakers et al. |
| 2012/0157758 A1 | 6/2012 | Dietz |
| 2013/0102836 A1 | 4/2013 | Millman |
| 2016/0203284 A1 | 7/2016 | Ouyang et al. |

OTHER PUBLICATIONS

American Academy of Pediatric Dentistry (AAPD) Clinical Affairs Committee. "Guideline on Behavior Guidance for the Pediatric Dental Patient." Clinical Practice Guidelines, Reference Manual (2015-2016), 37(6): 180-193.

Bandler, Richard, et al. "Brain mediation of active and passive emotional coping," Progress in Brain Research (2000), 122: 333-349.

Brock, C. et al. "Transcutaneous cervical vagal nerve stimulation modulates cardiac vagal tone and tumor necrosis factor-alpha," Neurogastroenterology & Motility (May 2017), 29(5): 1-4.

Collingwood, Jane. "The Power of Music to Reduce Stress," PsychCentral (Mar. 22, 2018). Retrieved from the Internet: https://psychcentral.com/lib/the-power-of-music-to-reduce-stress/.

Donnelly, Joe. "Experiencing 'Deep,' the Virtual Reality Game that Relieves Anxiety Attacks," Vice (Mar. 24, 2015). Retrieved from the Internet: https://www.vice.com/en_us/article/xd5em3/experiencing-deep-the-virtual-reality-game-that-relieves-anxiety-attacks-142.

Ellrich, Jens. "Transcutaneous Vagus Nerve Stimulation," European Neurological Review (Winter 2011), 6(4): 2-4.

Frangos, Eleni, et al. "Non-invasive Access to the Vagus Nerve Central Projections via Electrical Stimulation of the External Ear: fMRI Evidence in Humans," Brain Stimulation (2015), 8(3): 624-636.

Guelmann, Marcio. "Dental fear in children may be related to previous pain experience during dental treatment," J. Evid. Base Dent. Pract.(2005), 5(3): 143-144.

Keay, Kevin A. et al. "Parallel circuits mediating distinct emotional coping reactions to different types of stress," Neuroscience and Biobehavioral Reviews (Dec. 2001), 25(7-8): 669-678.

Milgrom, Peter, et al. "Origins of childhood dental fear," Behav. Res. Ther. (1995), 33(3): 313-319.

Steimer, Thierry. "The biology of fear- and anxiety-related behaviors," Dialogues in Clinical Neuroscience (2002), 4(3): 231-249.

Townend, Ellen, et al. "A clinical study of child dental anxiety," Behavior Research and Therapy (2000), 38(1): 31-46.

Vinkers, Christiaan H., et al. "The effect of stress on core and peripheral body temperature in humans," Stress (2013), 16(5): 520-530.

\* cited by examiner

DEVICES, SYSTEMS AND METHODS FOR INHIBITING OR DISRUPTING PEDIATRIC ANXIETY

CLAIM OF PRIORITY

This application is a continuation of non-provisional U.S. patent application Ser. No. 15/985,776, now U.S. Pat. No. 10,661,048, entitled "DEVICES, SYSTEMS AND METHODS FOR INHIBITING OR DISRUPTING PEDIATRIC ANXIETY" and filed on May 22, 2018, which claims the benefit of priority under 35 U.S.C. § 119(e) to U.S. Provisional Patent Application Ser. No. 62/509,342, entitled "DEVICES, SYSTEMS AND METHODS FOR INHIBITING OR DISRUPTING PEDIATRIC ANXIETY" and filed on May 22, 2017, both of which are herein incorporated by reference in their entirety.

TECHNICAL FIELD

Embodiments relate to devices, systems and methods for reducing anxiety in children undergoing medical, dental, or other procedures or novel situations that can cause anxiety.

BACKGROUND

Children who experience anxiety associated with novel situations react physically and emotionally in ways that make it challenging for the child, parents, educators, and providers to proceed with the intended goal of that novel situation. These situations can include starting school, going to the doctor, going to the dentist, and flying on a plane, for example. Any new situation can pose these challenges for children, and in particular for certain populations of children who are developmentally delayed, interact with the world around them differently because of heightened sensory awareness, or who have special needs. One specific example is in the setting of medical intervention where the child's reactions can make it challenging for care providers to administer the necessary treatment without physically or chemically restraining the child in a way that causes additional anxiety and further promotes negative associations with the treatment. For some children, anxiety can be caused leading up to a visit to a doctor, dentist, or other medical professional. Anticipatory anxiety can result in activation of the behavioral inhibition system, causing hippocampus activation and increased attention to novel environmental stimuli and heightened arousal.

To conduct a medical procedure, a caregiver may therefore provide sedatives or anesthetics. Additionally or alternatively, a caregiver may physically restrain an anxious child. A growing body of evidence from animal studies and observational studies in humans, however, suggests adverse effects on behavior, learning, and memory may result from exposure to anesthetics and sedation during periods of rapid brain development. In 2014, the International Anesthesia Research Society and U.S. Food and Drug Administration (FDA) convened a group of experts in anesthesia, pediatric medicine, neuroscience, and patient safety to consider the evidence and what it means for health care providers and parents. The FDA has subsequently issued guidelines to help healthcare professionals balance the benefits of appropriate anesthesia in young children against the potential risks. The SmartTots Consensus Statement on the Use of Anesthetic and Sedative Drugs in Infants and Toddlers is the result of many hours of deliberation by that diverse group of experts along with feedback from more than 20 stakeholder organizations. The feedback from these organizations indicates that children need an alternative peri-procedural approach in order to decrease anxiety, minimize use of anesthetics, and maximize patient outcomes.

SUMMARY

Devices, systems and methods described herein can reduce anxiety in children undergoing medical or dental procedures, for example. The reduction can be accomplished by fun, educational, or distracting stimuli at key stages corresponding to a medical or dental procedure. The stimuli introduced can familiarize a child with the environment in which the procedure will take place and the equipment and people which the child will meet. By using consistent stimuli, and by disrupting anxiety at one or more of a series of stages in which anxiety typically occurs, a reduction in needed anesthesia can be achieved, which is healthier for the child and reduces the costs associated with the medical or dental procedure.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail below. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Devices, systems and methods described herein can reduce anxiety in a patient, particularly a child, by inhibiting the initiation and/or progression of neural anxiety pathways. These devices, systems and methods use consistent, expected stimuli at various stages of the pre-procedure, procedure, and post-procedure stages.

Figure 1:
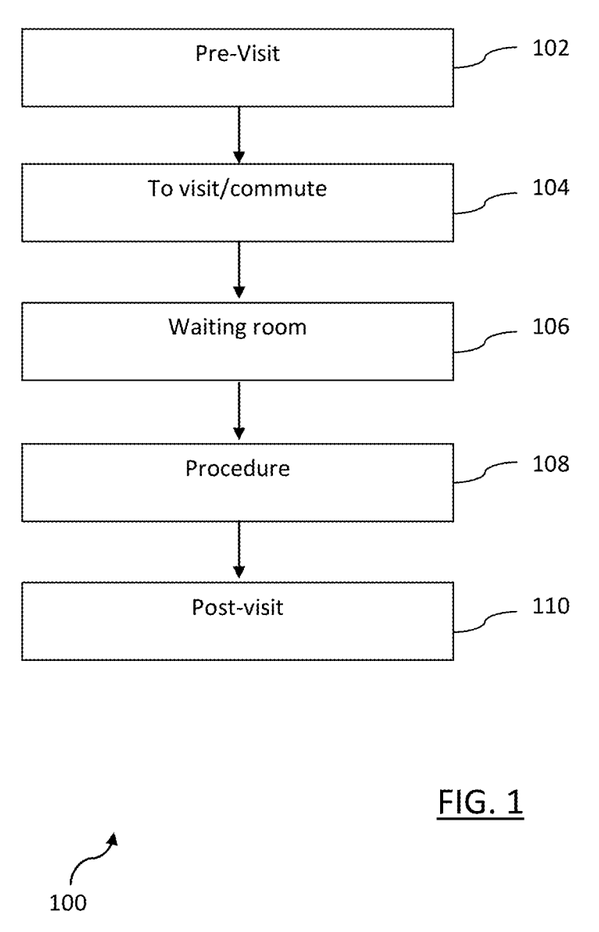
FIG. 1 is a flow chart depicting stages at which pediatric anxiety can be addressed according to embodiments.

FIG. 1 is a flowchart depicting the various stages of a typical procedure pathway 100. As shown in FIG. 1, procedure pathway 100 includes a pre-visit stage 102, a commute stage 104, a waiting room stage 106, a procedure stage 108, and a post-visit stage 110. The stages 102-110 shown in FIG. 1 are generally conducted in sequence. Furthermore, each of the stages 102-110 presents a potential for the child to become anxious, which is detrimental to the child and possibly the outcome of the visit.

For example, a child may undergo a dental checkup. Pre-visit stage 102 corresponds to the time before traveling to the dental office. A child can become anxious regarding the dental checkup when informed about the upcoming dental checkup. Especially in situations where the child is unfamiliar with what will happen during a dental procedure, or where the office is unfamiliar, learning about an upcoming visit can produce anxiety.

Next, typically on the day of the procedure, the commute stage 104 occurs, in which the child travels to the location of the procedure. Then the child waits for the procedure to begin during the waiting room stage 106, and the procedure itself occurs during the procedure stage 108. Finally, a post-visit stage 110 corresponds to the time period after the procedure is complete, which can be either in a recovery area or at a location outside of the clinic, such as at home, depending upon the procedure.

In alternative embodiments, additional stages may be present, such as an in-clinic post-visit stage. Depending upon the type of medical, dental, or other event that can produce anxiety in a child, various other preparatory, procedure, or post-procedure stages can exist in procedure pathway 100.

In embodiments, anxiety is reduced by addressing at least four focus areas. Those focus areas are (1) anxiety produced during the pre-visit stage 102, (2) anxiety produced at the waiting room stage 106, (3) anxiety produced at the procedure stage 108, and (4) anxiety produced at the post-visit stage 110. It will be understood that in alternative embodiments, similar anxiety-reducing steps could be taken at various other stages throughout procedure pathways of other embodiments. In general, reduction of anxiety is beneficial at all stages for young patients. To reduce overall anxiety and improve outcomes and reduce the need for anesthetics, however, it is believed that addressing anxiety at these four focus areas is particularly effective. That is because, at these focus areas, several key central neural pathways can be modulated by utilizing specific sensory inputs that are non-invasive and do not require anesthetics.

Pre-visit stage 102 can result in anxiety when a child learns about an upcoming procedure. For example, a parent or other adult may tell a child at pre-visit stage 102 that an upcoming visit to a medical professional will not hurt, or that it will not be too bad. The child may respond to this by wondering why they are being reassured about something, and assume that the procedure will in fact be painful or distressing. In order to prevent anticipatory anxiety intervention at pre-visit stage 102, embodiments can be targeted at minimizing the activation of the behavioral inhibition system. In embodiments, the behavioral inhibition system can include hippocampus activation and/or novel stimuli. Another target can include decreasing locus ceruleus activation at stages 102, 104, 106 and/or 108.

Furthermore, in order to build a pathway (e.g., pathway 100 of FIG. 1) to address anxiety throughout the entire process corresponding to a medical procedure, stimuli can be employed that are consistent with stimuli used throughout the rest of the pathway 100. Such consistent stimuli can be one of a variety of types, such as sounds, sights, or interactive characters that are used consistently in other stages of the pathway 100. In an example, the character is the consistent theme that bridges two unrelated stages or other environments of the pathway 100. This consistency negates novelty of the clinical setting.

In embodiments, consistent stimuli can increase predictability and reduce the surprise factor corresponding to the pathway 100. For example, at pre-visit stage 102, a child can be introduced to images or explanations related to the actual clinic, hospital, dental office, or other location which he or she will be visiting. Likewise, stimuli such as characters, games, or sounds can be introduced at the pre-visit stage 102 which will be revisited again at later stages of pathway 100. In embodiments, the stimuli can be customized to a patient, including his or her name, the clinic or hospital the patient will be visiting, and information regarding the specific procedure that the patient will be undergoing. In some embodiments, a photograph or other image corresponding to the location such as the waiting room, a dental chair, or images of the doctors, nurses, or other staff at the location of the procedure can be provided on a screen for the child. Additionally or alternatively, information can be provided regarding how long the procedure will take or what will be involved in the procedure. In embodiments, tutorials, games, or examples can be provided for the child to practice. Furthermore, stimuli can be provided to familiarize the child with what they will experience during the procedure. For example, the sounds of a drill tool can be provided, along with an explanation of what a fluoride treatment is or when it will happen during the procedure. In this way, the stimuli that the child will experience during the procedure are already familiar and the level of anxiety experienced during the procedure is reduced.

The second focus area is at the waiting room stage 106 of FIG. 1. At waiting room stage 106, additional stimuli can be provided that increases the predictability of the environment and reduces surprises associated with the process. Whereas the stimuli provided at the pre-visit stage 102 can be informative of preparatory, stimuli at the waiting room stage 106 can enhance the welcoming or fun nature of the office setting. Like the stimuli provided at pre-visit stage 102, the stimuli provided at waiting room stage 106 can reduce activation of the hippocampus with novel stimulus, as well as reducing activation of the hypothalamus to cause corticotropin-releasing hormone (CRH) cascade. This stimulation can reduce hypothalamic pituitary adrenal axis activation with waiting room activities. Such activities can include sensory inputs such as music or a calming voice tone, in embodiments. Devices or systems can provide vagus nerve stimulation to decrease a level of anxiety, in some embodiments. For example, such devices can be placed in or on the ear to provide vagus nerve stimulation.

The third focus area is the procedure stage 108 of FIG. 1. At procedure stage 108, additional stimuli can be provided that increases the predictability of the environment and reduces surprises associated with the process. As with waiting room stage 106, additional stimuli can be provided to enhance the welcoming or fun nature of the procedure. Like the stimuli provided at pre-visit stage 102 and waiting room stage 106, the stimuli provided at procedure stage 108 can reduce activation of the hippocampus with novel stimulus. Furthermore, as with waiting room stage 106, the stimuli can reduce activation of the hypothalamus to diminish the corticotropin-releasing hormone (CRH) cascade. Finally, the stimuli provided at procedure stage 108 can activate the vagus nerve to provide a distraction from the actual procedure and reduce anxiety.

Finally, the fourth focus area occurs at post-visit stage 110. At this stage, stimuli can be provided to disrupt anxiety relating to future visits and reinforce good behavior.

Throughout each of these four focus areas, consistent stimuli are provided such that the child undergoing a treatment or other procedure is immersed by familiar sensory environments. Additionally, the stimuli can distract from more upsetting sounds or sights, in embodiments. The stimuli can be entertaining or fun for the child, as well as explaining why the procedure or treatment is happening (for example, to keep him or her from getting sick, or to prevent cavities).

The stimuli described above can be provided in a variety of ways. For example, in one embodiment the stimuli can be provided via a smartphone, tablet device, TV, or other screen. In such embodiments, there can also be audio stimuli. In some embodiments, such as procedures associated with sounds that could induce anxiety, headphones, ear buds, or bone conduction can be used to provide the stimuli, and also block out those other sounds. Examples of such procedures include dental procedures or magnetic resonance imaging (MRI).

In still further embodiments, it may be desirable to create a virtual reality (VR), augmented reality (AR), or mixed reality (MR) environment. Such environments can be, for example, provided on a smartphone screen. In other embodiments, the VR/AR/MR environment can be produced using a VR headset or glasses. In some embodiments, a combination of audio and visual systems can be used to produce the desired stimuli.

The consistent stimuli could be, for example, a character. In one embodiment, a character introduces the child to the waiting room and the procedure during the pre-visit stage 102. At the waiting room stage 106, the character may be found using VR/AR/MR, or there may be a physical version of the character at the waiting room. In an example, the character is overlaid on non-fiction footage to create a MR. Alternatively, the character takes non-fiction objects and incorporates them into fictional environments, such as by using procedural equipment on the character in a manner similar to how a clinician would use the equipment on a patient. Likewise, during the procedure stage 108, the character may be present either in a physical instantiation or in a VR/AR/MR sense.

Figure 2:
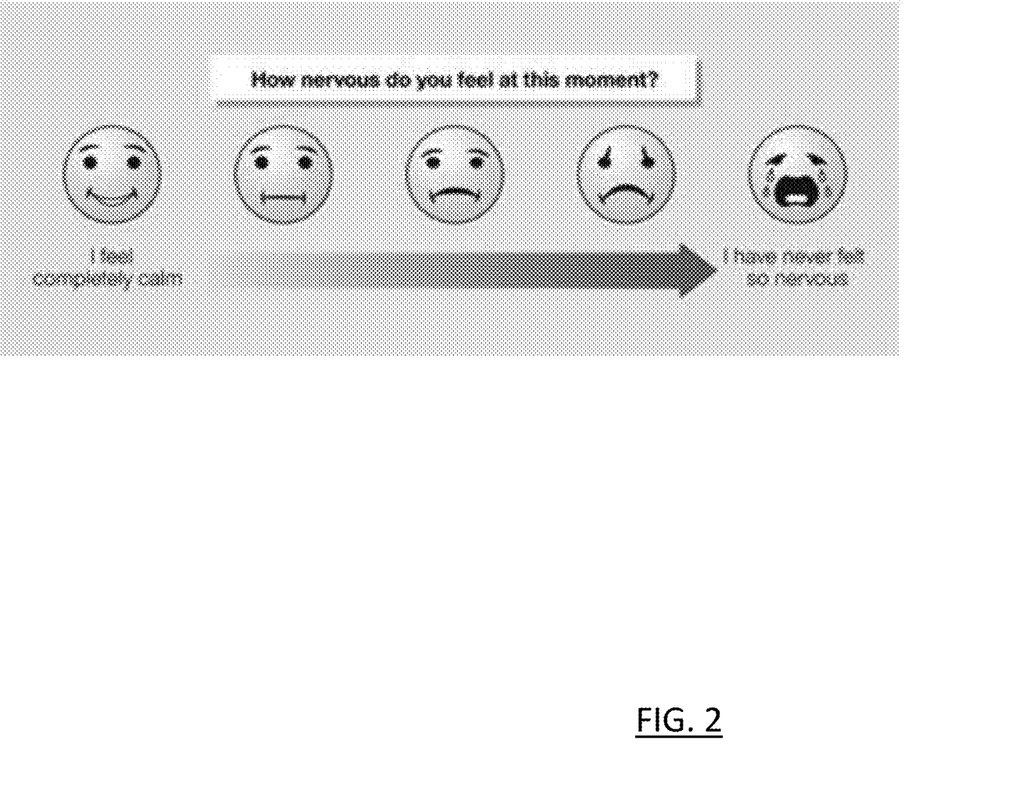
FIG. 2 depicts a scale that can be used by a child to indicate a level of nervousness according to an embodiment.

FIG. 2 is an example of a sliding scale that can be used by a child in embodiments to provide feedback regarding their level of anxiety. Depending upon the level of anxiety reported by the child, the system can provide different stimuli. For example, if a child is becoming more anxious, then additional distracting, calming, or fun stimuli could be provided in a closed loop manner. Among some populations of children, such as children with autism or related disorders, tactile therapy (deep touch pressure) can reduce anxiety. Tactile therapy can include weighted clothing or other sources of pressure. In embodiments, tactile therapy can be applied at predetermined locations that are known to cause a decrease in anxiety. Tactile therapy could also be incorporated so that the deep touch pressure delivery mechanism responds to increased anxiety levels by increasing frequency or amplitude of the pressure, in embodiments. In embodiments, a level of anxiety is not directly reported. Rather, differences in pulse rate, breathing rate, salivation, or other physiological changes (pupil dilation, sweating, temperature, or other factors) can be detected by the system via biosensors and an appropriate stimulus could be provided specific to each patient. This could be achieved with machine learning to identify successful strategies for reducing anxiety in each patient to provide personalized medicine. Machine learning can be based on a specific patient, or can be based on an aggregate of patients of a like demographic, for example.

In embodiments, the system can provide different stimuli at different stages of a procedure. For example, during a dental visit, different stimuli could be provided during the checkup inspection and during scraping or polishing. Polishing, for example, may be louder and a system may provide auditory stimuli such as music or a calming voice that will distract from that noise. The voice or music can vary in type, tone, volume, and/or cadence based upon the stage of the procedure and/or the level of anxiety in the patient.

FIGS. 3A-3H show one particular embodiment of a system for introducing a patient to a clinical environment. The system shown in FIGS. 3A-3H and other embodiments encompass specific colors, cadence, volume, smells, animations, and phrases that are specifically targeted to have a soothing effect. As such, systems described herein can be used to decrease anxiety of a child during a medical visit by coaching the child. Furthermore, as shown in FIGS. 3A-3H, systems can be configured to gamify the process of a visit to a doctor or dentist, including incentivizing the child with reward based system.

Figure 3A:
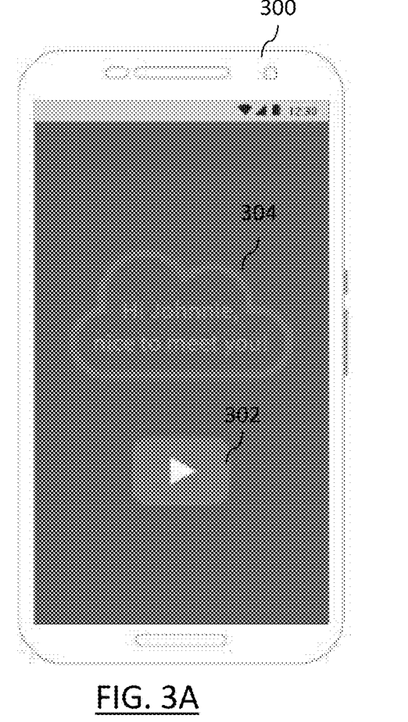
FIGS. 3A-3H depict a peri-procedural system for addressing anxiety according to an embodiment.

As shown in FIG. 3A, an app is provided on a smartphone 300. The app depicts a start button 302 as well as a greeting 304. In the embodiment shown in FIG. 3A, the greeting is personalized to the child who will be undergoing a procedure.

Figure 3B:
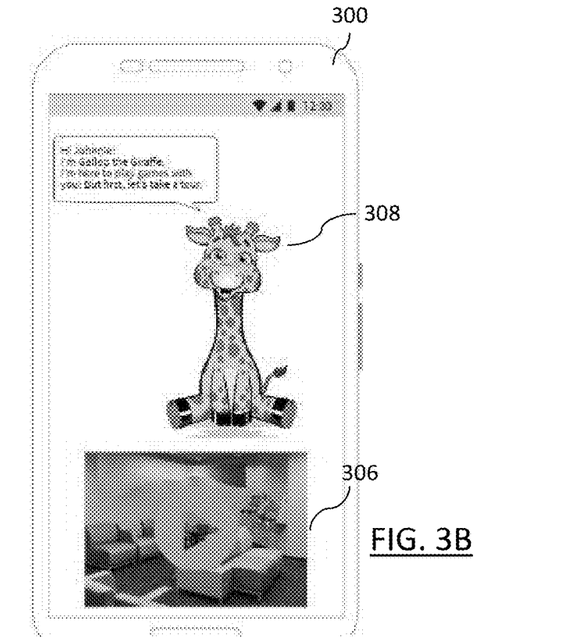

As shown in FIG. 3B, an introduction screen is provided on smartphone 300. The introduction screen shown in FIG. 3B can be provided at the pre-visit stage (e.g., pre-visit phase 102 of FIG. 1) in embodiments. The stimuli provided at this stage can be used to familiarize a child with the office, clinic, or hospital that he or she will be visiting. Furthermore, the stimuli provided at this stage can be consistent with stimuli that will be provided at other stages.

For example, the stimuli used to familiarize the child with the office, clinic, or hospital, including the care providers that he or she will be visiting is shown in FIG. 3B as video 306. Video 306 is a video that shows the child what the office waiting room looks like. In alternative embodiments, additional videos or pictures can depict other parts of the location where the procedure will take place, to familiarize the child with the procedure that will take place.

The stimuli that will be consistent with other stimuli provided at other stages of the procedure can also include VR/AR/MR features. For example, as shown in FIG. 3B, a character 308 can be introduced during the pre-visit stage. Character 308 can be used to convey information, but also to provide games, distractions, and generally be fun for the child to interact with and to reduce levels of anxiety.

Figure 3C:
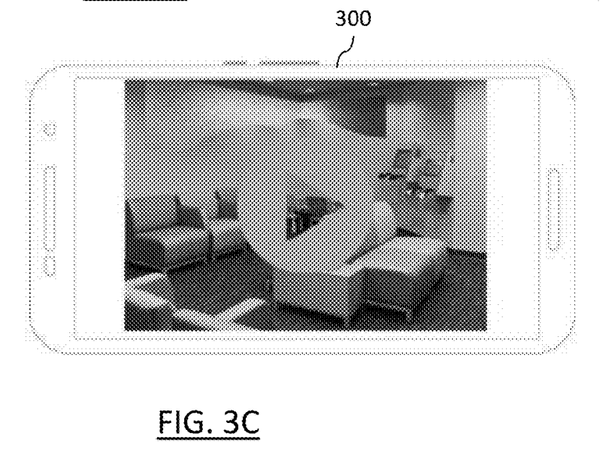

FIG. 3C shows video 306 is more detail. After an introduction from character 308 as shown in FIG. 3B, video 306 can be displayed across the entire screen of smartphone 300. In alternative embodiments, rather than smartphone 300 the introduction video could be provided on a television or a headset. In other embodiments, photos or games could be provided rather than a video to introduce various parts of the office or procedure facilities.

Figure 3D:
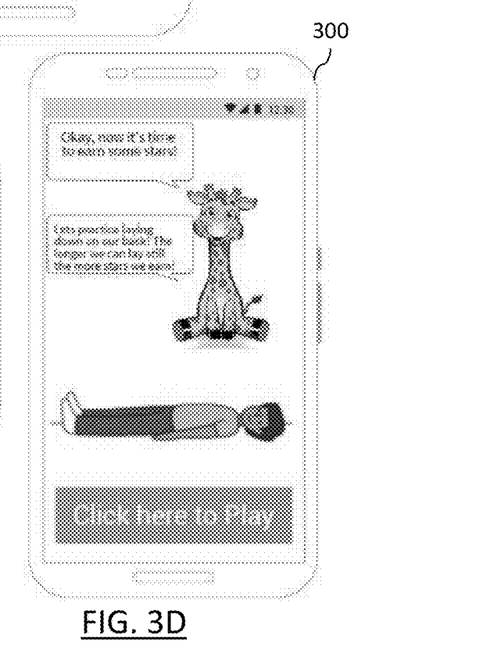

As shown in FIG. 3D, a game is provided on smartphone 300. In FIG. 3D, stars, points, or other rewards are introduced based on a child playing a game that corresponds to the procedure he or she will undergo. In embodiments, depending on a number of points or stars that the child earns, the child can earn prizes from a caregiver, parent, or the provider of the app. In the embodiment shown in FIG. 3D, stars are awarded for practicing lying down on one's back for a period of time. This may familiarize the child with the necessary procedures for undergoing an MRI exam, for example. FIG. 3D shows the number of stars earned by a child for completing the practice task.

Figures 3E, 3F, 3G, 3H:
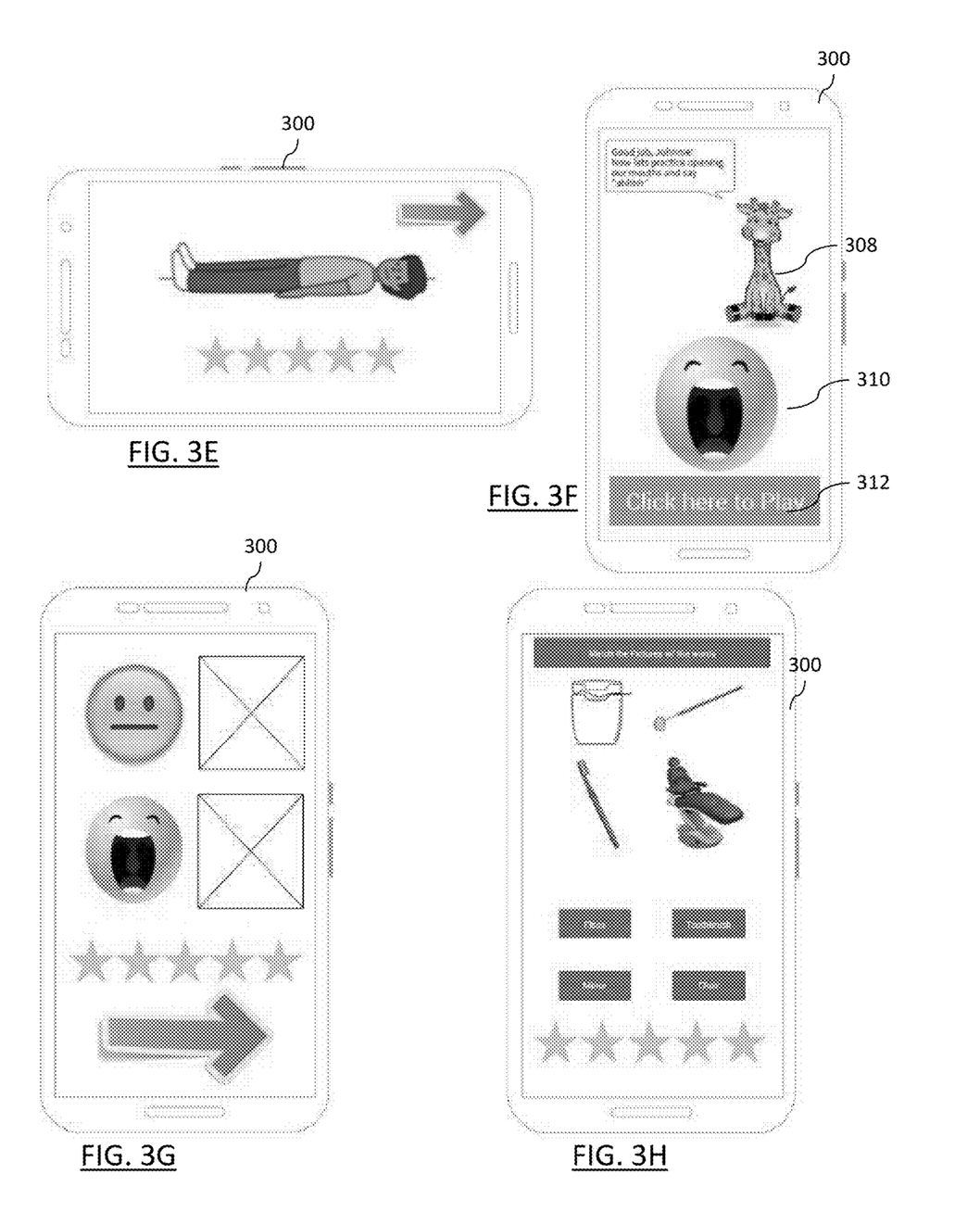

FIG. 3F shows a second gamified task for additional stars. In addition to character 308, FIG. 3F also includes an emoji or other graphical feature that shows a child how to complete a particular task in a fun way. For example, in FIG. 3F, emoji 310 shows a child how to open his or her mouth while character 308 provides more details on how to prepare for a dental visit. Here, the child is asked to provide audio feedback by saying "ahhhh," just as a dentist likely would ask a child to do for a dental checkup. In order to detect whether the child is doing this correctly, start button 312 can be pressed and the smartphone 300 can detect how well and for how long the child carries out the task. In varying examples, a clinician can provide a request to a device or system in real-time, and the device or system can cause the character to provide an instruction to the patient to complete a certain action or task. For instance, Dr. Dentist can say, "Okay hygienist, it's time to count teeth." The device or system can receive and analyze the "count teeth" command, and then cause the character to instruct the patient, via video and/or audio means, to open his/her mouth and say "ahhhh."

FIG. 3G shows stars associated with opening and closing as one would at the dentist.

FIG. 3H shows a gamified system for identifying the items that the child will encounter at a dental office. This gamified system provides at least two benefits. First, the child learns what items he or she is likely to encounter at the dentist, which makes the stimuli at the dental office less anxiety-inducing. Second, the process is gamified with additional stars so that the items are associated with the prizes and the anxiety-inducing nature of those items is reduced.

At the time of the office visit, these and other games and stimuli can be provided to entertain, distract, or otherwise break the anxiety-producing patterns that are associated with the visit. Furthermore, in embodiments where a child becomes familiar with a particular character 308 it may be desirable to use that character 308 to teach the child about more than one type of office visit. For example, the giraffe character 308 shown in FIGS. 3A-3H is used to teach a child about a dental visit, but could also be used to teach the same child about a wellness check at a doctor's office, or other types of medical procedures.

Figure 4:
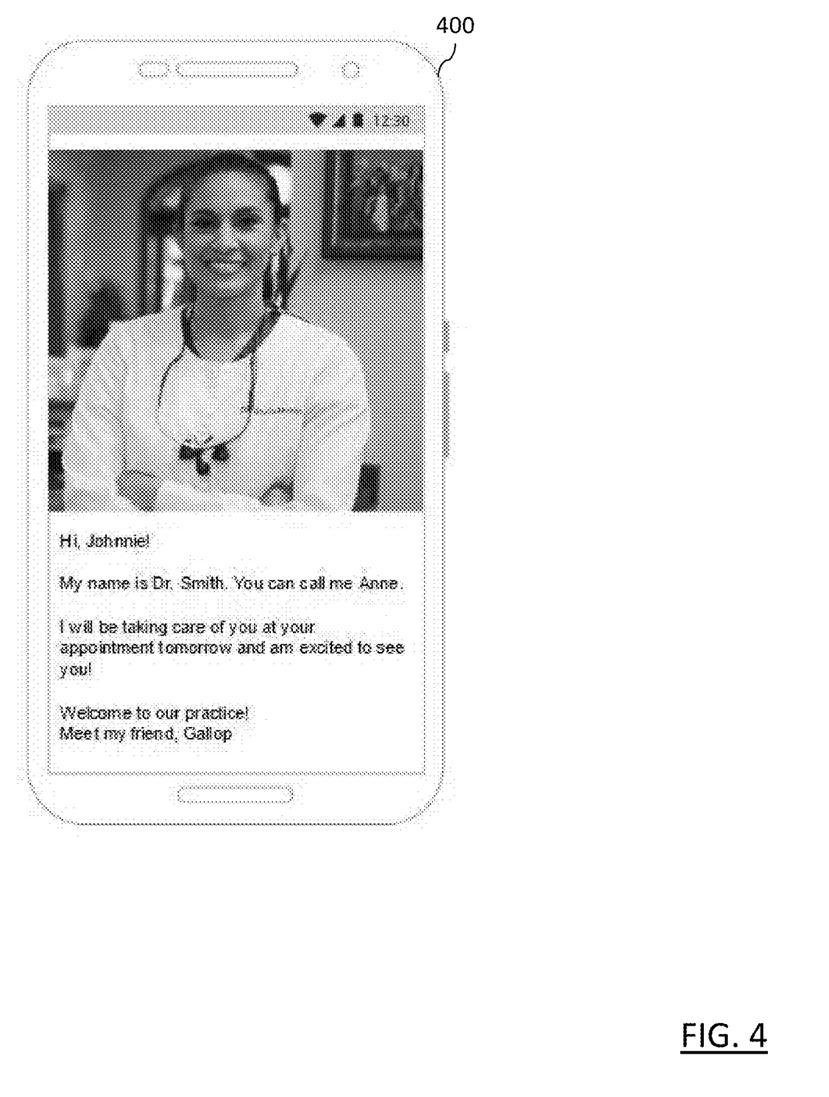
FIG. 4 depicts an introduction and familiarization display according to an embodiment.

FIG. 4 is an example of an alternative type of display that can be used to familiarize a patient with aspects an upcoming procedure, disrupting neural anxiety pathways. As previously described with respect to FIGS. 3B and 3C, for example, aspects of the physical location of a procedure or checkup can be provided to the patient in embodiments. Likewise, as shown in FIG. 4, the staff, doctor, surgeon, or other people with whom the patient will be meeting can be introduced via smartphone 400 or other displays.

Figure 5:
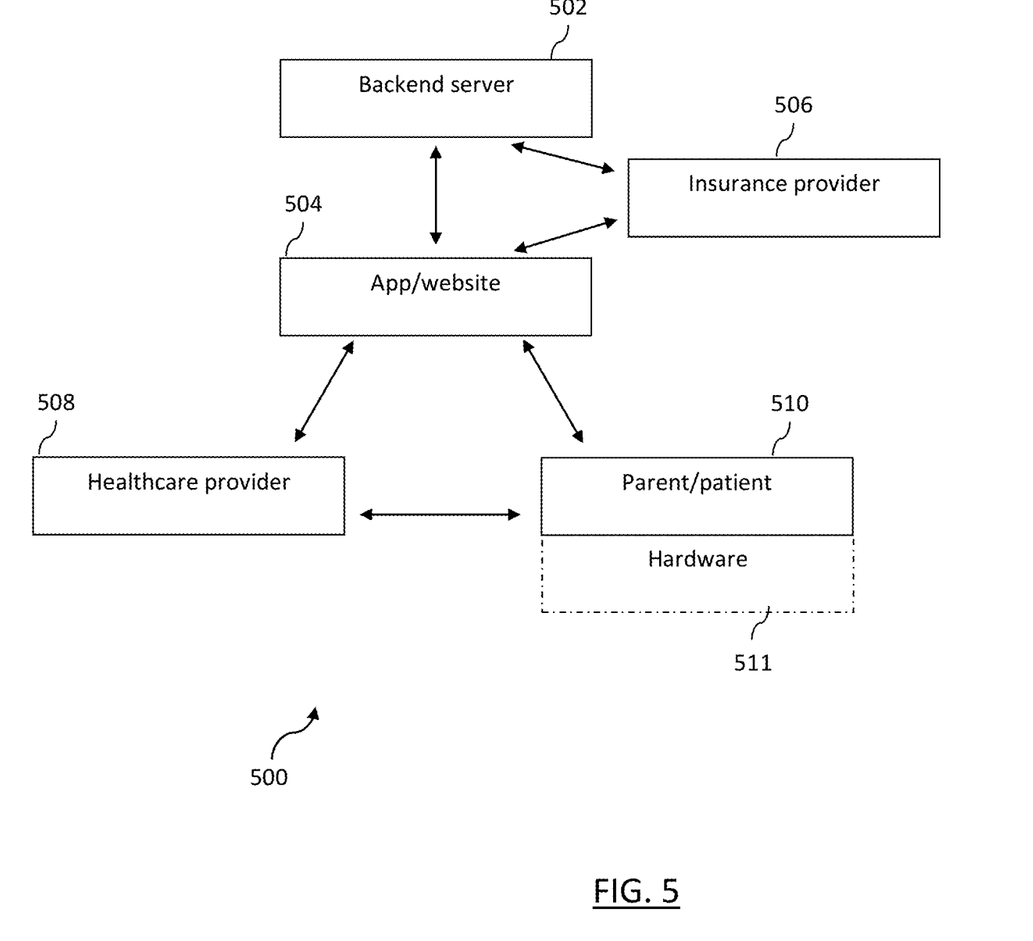
FIG. 5 depicts a system including a backend component and user device according to an embodiment.

FIG. 5 depicts system 500 according to an embodiment. System 500 is a network of communicative interactions between a backend server 502, an application program interface (API, or "app") and/or website 504, a computer system or server of an insurance provider 506, a computer system or server of a healthcare provider 508, and computing device of a patient or parent 510. In the embodiment shown in FIG. 5, the app or website 504 is a central node through which communication can occur between the backend server 502, insurance provider 506, healthcare provider 508, and patient or parent 510. App or website 504 can be an interface with a company or provider of the service, in embodiments.

Hardware 511 is shown in dashed lines because it is optional. In embodiments, hardware 511 can include a physical device on or near parent or patient 510. For example, hardware 511 can include a VR headset or glasses, as described above. Alternatively, hardware 511 can include some object that the parent/patient 510 interacts with at healthcare provider 508. For example, hardware 511 can be a wall decal or activity station that is present at healthcare provider 508. In embodiments, hardware 511 can be interactive via VR headset or glasses, or through some other virtual or augmented reality system. In other embodiments, hardware 511 that is present at healthcare provider 508 can be interactive without the use of virtual or augmented reality systems.

In other embodiments, system 500 can include additional components or entities, omit one or more of the depicted components or entities, and/or include additional communicative or other relationships (e.g., insurance provider 506 can be communicatively coupled with healthcare provider 508) beyond those specifically depicted in the example embodiment of FIG. 5.

Backend server 502 is a system of one or more servers or other devices and operates the various features and components described above with respect to FIGS. 1-4. For example, backend server 502 can store information regarding a schedule of upcoming visits to one or more healthcare providers 508 by one or more patients 510. Backend server 502 can schedule the games, points, training, and other features described above for patients 510 at appropriate times in order to disrupt neural anxiety pathways that might otherwise be affected by a visit to a healthcare provider 508. Furthermore, backend server 502 can communicate with insurance provider 506, in embodiments, to manage information that could be relevant to that provider. For example, in embodiments the disruption of an anxiety pathway can reduce the need for personnel, equipment, and supplies associated with anesthesia, which may result in reduced costs for a medical procedure. Where a medical procedure is less expensive due to use of app or website 504 running an anxiety-disrupting system proscribed by backend server 502, insurance provider 506 may reduce the costs to parent or patient 510 or may provide some benefit to healthcare provider 508 associated with reducing those costs.

App or website 504, as described above with respect to FIGS. 1-4, can provide customized information, games, and training as described above for each parent or patient 510. In embodiments, app or website 504 can be accessible by a variety of platforms. For example, app or website 504 can be available through an instance of the app on the smartphone or tablet of a particular patient 510. The same app or website, or similar information, training, and/or games that are likewise customized to the patient 510, can be accessible via a computer monitor, or at the facilities of the healthcare provider 508 or providers associated with patient 510.

Insurance provider 506 can interact with backend server 502 and/or website 504, in embodiments. In further embodiments, insurance provider 506 can communicate directly with healthcare provider 508. Insurance provider 506 (or another entity) can provide incentives for patients/parents 510 and/or healthcare providers 508 to use app/website 504. These incentives can promote use of the anxiety-disrupting technologies described above, which in turn can reduce costs and poor outcomes associated with anesthesia or unnecessarily stressed patients.

Healthcare provider 508 can also interact with app/website 504 in order to proscribe certain types of anxiety-pathway disruption for parents/patients 510. Healthcare providers 508 can, in embodiments, proscribe use of app/website 504 at various time points associated with anxiety disruption and corresponding to the schedule of visits for parent/patient 510. For example, healthcare providers 508 can provide information or games on the day of a visit, a day before a visit, a week before a visit, or at other key times to disrupt neural anxiety pathways. In some embodiments, as indicated by the arrow between healthcare provider 508 and parent/patient 510, communication can occur directly between those two entities rather than passing through app/website 504. For example, notifications about upcoming appointments can be provided directly to parent/patient 510 from healthcare provider 508 in embodiments.

In embodiments, system 500 and/or its components or sub-systems can include computing devices, microprocessors, modules and other computer or computing devices, which can be any programmable device that accepts digital data as input, is configured to process the input according to instructions or algorithms, and provides results as outputs. In an embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

In embodiments, a medical device can be connected to the app or website, and can interact with the software or solution for reducing anxiety. The solution or process can input patient data from electronic health records, or from manual entry from point of care sites and/or parents via the website or app, in embodiments. In turn, the solution or process can output notifications to patients, or can output data that is generated and gathered, or tracking of accomplishments of an incentive program as described above.

In embodiments, the initial interaction between a healthcare provider and the patient or parent is to set up an appointment. At a set time prior to the appointment, a notification can be sent by text message, app notification, email, or some other notification mechanism. Prior to notification, in embodiments, patient data is entered into the solution or process framework.

Prior to the procedure, a healthcare provider can input electronic health record data via sync or manual entry. This data can be used to personalize the system, for example by having the app include the patient's name or other personalized content.

Pre-procedure, such as in a waiting room, the system can be accessed by the healthcare provider to send a notification to the parent or patient. The system, such as by way of an app, can be coupled to a smartphone microphone and camera to facilitate interaction with the patient. Interactive functions can award stars, points, or other rewards for good compliance. Other game type of functions can be implemented to prepare a patient for his or her procedure, as described above. At the point of care site, in embodiments, the patient can continue to use the system either on a smartphone or other device owned by the patient/parent, or on a tablet or other device that is kept by the healthcare facility.

During the procedure, the physician or other health professional can utilize functions of the system to hand out "stars" or other rewards for good behavior. In embodiments, audio (including audio customized to include the patient's name or other information) can be associated with additional rewards, points, or stars.

After the procedure, a notification can be sent to the patient that summarizes the visit. For example, in embodiments the summary can include details on how many stars were earned, or a message from the healthcare provider, or follow-up information.

In embodiments, a system can be used for multiple anxiety-inducing events. For example, a particular patient can interact with the systems described herein prior to visiting a dental office, a doctor's office, before a flight, before a first day of school, before a test, or other like event that can create anxiety. The system can have common features between each of these events. For example, the character-based system shown in FIGS. 3A-3H could be employed in each of these scenarios and others, using the same or a similar character. Likewise, similar points, stars, games, and information delivery style can be used for the same child between several different instantiations of a common system for a single patient.

In addition to these commonalities, a system for any given patient or group of patients can change. For example, in embodiments a single child may use a system as described herein for a variety of events over a course of time. As the child becomes older, the features of the system can update to match the development of the child. For example, games that are suitable for a younger child may not be appropriate for an older child. Thus, as a child using a system described herein gets older, the games presented to disrupt anxiety pathways can change to be age-appropriate.

The systems described herein can include some elements (e.g., a character, a points or stars tracking system, an information presentation format) which remain consistent and predictable between anxiety-inducing events over time, and some elements (e.g., games) that update or change with the age or developmental progress of the patient. Additionally, the types of games, AR or VR features, and characters can change depending on the type of potentially anxiety-inducing event.

Computing and other devices discussed herein can include memory. Memory can comprise volatile or non-volatile memory as required by the coupled computing device or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

In embodiments, the system or components thereof can comprise or include various modules or engines, each of which is constructed, programmed, configured, or otherwise adapted, to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of devices, systems and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions. Thus, the following claim examples are hereby incorporated into the detailed description, with each example standing on its own as a separate embodiment:

In Example 1, a method for minimizing anxiety, such as anticipatory anxiety, in a child undergoing a medical or dental procedure can comprise modulating the child's neural anxiety pathways by providing consistent-themed stimuli at a time before the procedure, during the procedure, and after the procedure. The stimuli can familiarize the child with an environment in which the procedure will take place or equipment and people which the child will meet.

In Example 2, the method of Example 1 can optionally further comprise receiving an indication of the child's level of anxiety, and formulating a program for modulation of the child's neural anxiety pathway based on the indication.

In Example 3, the method of Example 2 can optionally be configured such that receiving the indication of the child's level of anxiety is received as an input from the child.

In Example 4, the method of Example 2 can optionally be configured such that receiving the indication of the child's level of anxiety is extrapolated based on changes to one or more of the child's heart rate, pupil dilation, respiratory rate, vocalization level, or muscle tension.

In Example 5, the method of any one or any combination of Examples 1-4 can optionally be configured such that modulating the child's neural anxiety pathways includes inhibiting or disrupting the initiation and progression of the child's neural anxiety pathways.

In Example 6, the method of Example 5 can optionally be configured such that inhibiting or disrupting the initiation and progression of the child's neural anxiety pathways includes minimizing activation of the child's behavioral inhibition system.

In Example 7, the method of Example 6 can optionally be configured such that minimizing activation of the child's behavioral inhibition system includes minimizing hippocampus activation, locus ceruleus activation, or hypothalamus activation.

In Example 8, the method of any one or any combination of Examples 1-7 can optionally be configured such that modulating the child's neural anxiety pathways includes minimizing an amount of anesthesia given to the child during the procedure.

In Example 9, the method of any one or any combination of Examples 1-8 can optionally be configured such that providing the stimuli at the time before the procedure includes providing the stimuli at a location distinct from a clinic at which the procedure will take place, during the commute to the procedure, and in the waiting room of the clinic.

In Example 10, the method of any one or any combination of Examples 1-9 can optionally be configured such that providing the stimuli includes utilizing non-invasive sensory inputs.

In Example 11, the method of any one or any combination of Examples 1-10 can optionally be configured such that providing the stimuli includes delivering one or more sounds, sights or smells to the child.

In Example 12, the method of Example 11 can optionally be configured such that delivering the one or more sounds, sights or smells to the child includes utilizing a smartphone, tablet device or TV.

In Example 13, the method of Example 11 or 12 can optionally be configured such that the sights include images of one or more of the waiting room of the clinic at which the procedure will take place or doctors, nurses or other staff at the clinic.

In Example 14, the method of Example 13 can optionally be configured such that the sights further include an image of a character in addition to the waiting room of the clinic at which the procedure will take place or doctors, nurses or other staff at the clinic. The character can be overlaid on non-fiction footage to create a mixed reality, or the character can take non-fiction objects and incorporate the objects into a fictional environment. In some examples, the character is the consistent theme that bridges two or more unrelated environments and provides a soothing reference for the child.

In Example 15, the method of any one or any combination of Examples 11-14 can optionally be configured such that the sounds include sounds associated with equipment to be used during the procedure.

In Example 16, the method of any one or any combination of Examples 1-15 can optionally be configured such that providing the stimuli includes providing vagus nerve stimulation to the child. The vagus nerve stimulation can come in various forms, including direct or indirect electromagnetic stimulation, pressure or tactile sensation, or breathing exercises. The vagus nerve can also be stimulated through any of its branches, such as Arnold's nerve.

In Example 17, the method of any one or any combination of Examples, 1-16 can optionally be configured such that providing the stimuli includes utilizing augmented, virtual, or mixed reality features.

In Example 18, the method of any one or any combination of Examples 1-17 can optionally be configured such that providing the stimuli includes instructing the child to perform a physical task, and a device or system recognizes completion of such task. To reinforce the stimuli and increase its familiarity, the physical task can be repeated one or more times.

In Example 19, the method of any one or any combination of Examples 1-18 can optionally be configured such that providing the stimuli includes providing an interactive tutorial or game for the child that explains why the procedure is beneficial.

In Example 20, the method of any one or any combination of Examples 1-19 can optionally be configured such that providing the stimuli includes providing customized stimuli to the child.

In Example 21, the method of Example 20 can optionally be configured such that providing the customized stimuli to the child includes using one or more of the child's name, the name of a clinic the child will be visiting, or information regarding the procedure that the child will be undergoing.

In Example 22, the method of any one or any combination of Examples 1-21 can optionally be configured such that providing the stimuli includes distracting the child from procedural sights or sounds.

In Example 23, the method of any one or any combination of Examples 1-22 can optionally further comprise providing tactile therapy to the child.

In Example 24, the method of any one or any combination of Examples 1-23 can optionally further comprise reinforcing good behavior by the child via a reward program.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A method for minimizing anxiety in a child, comprising:
    modulating the child's neural anxiety pathways by providing consistent-themed stimuli at a time before an anxiety-producing event,
    wherein the stimuli familiarizes the child with one or more of an actual environment associated with the anxiety-producing event, an actual piece of equipment associated with the anxiety-producing event, or an actual person which the child will encounter during the anxiety-producing event, and
    wherein providing the stimuli at the time before the anxiety-producing event includes providing the stimuli at a location distinct from a facility associated with the anxiety-producing event.

2. The method of claim 1, further comprising modulating the child's neural anxiety pathways by providing the consistent-themed stimuli at the facility associated with the anxiety-producing event.

3. The method of claim 1, further comprising modulating the child's neural anxiety pathways by providing the consistent-themed stimuli during the anxiety-producing event.

4. The method of claim 3, wherein providing the stimuli during the anxiety-producing event includes distracting the child from sights or sounds associated with the anxiety-producing event.

5. The method of claim 1, further comprising modulating the child's neural anxiety pathway by providing the consistent-themed stimuli at a time after the anxiety-producing event to disrupt anxiety relating to a similar future anxiety-producing event.

6. The method of claim 1, further comprising:
    receiving an indication of the child's level of anxiety; and
    formulating a program for modulation of the child's neural anxiety pathway based on the indication.

7. The method of claim 6, wherein receiving the indication of the child's level of anxiety is received as a manual input to an anxiety scale directly from the child.

8. The method of claim 6, wherein receiving the indication of the child's level of anxiety is extrapolated based on changes to one or more of the child's heart rate, pupil dilation, respiratory rate, vocalization level, or muscle tension.

9. The method of claim 6, wherein an aspect of the provided stimuli changes based on a change to the received indication of the child's level of anxiety.

10. The method of claim 1, wherein providing the stimuli includes delivering one or more sounds, sights or smells to the child.

11. The method of claim 10, wherein delivering the one or more sounds, sights or smells to the child includes utilizing a smartphone, a tablet device, a headset, virtual reality eyewear, or a TV.

12. The method of claim 10, wherein the sights include images of one or more of the actual environment associated with the anxiety-producing event, the actual piece of equipment associated with the anxiety-producing event, or the actual person which the child will encounter during the anxiety-producing event.

13. The method of claim 10, wherein the sounds include isolated sounds associated with the actual piece of equipment associated with the anxiety-producing event.

14. The method of claim 1, wherein providing the stimuli includes utilizing a fictional cartoon character.

15. The method of claim 1, wherein providing the stimuli includes instructing the child to perform a task to practice for a similar task the child will experience during the anxiety-producing event.

16. The method of claim 1, wherein providing the stimuli includes providing an interactive tutorial or game for the child that conveys why the anxiety-producing event is beneficial.

17. The method of claim 1, wherein providing the stimuli includes providing customized stimuli to the child.

18. The method of claim 17, wherein providing the customized stimuli to the child includes using one or more of the child's name or the name of the person which the child will encounter during the anxiety-producing event.

19. The method of claim 1, further comprising reinforcing good behavior by the child via a reward program.

20. The method of claim 1, wherein the anxiety-producing event is a visit to a dental office, a visit to a doctor's office, an air transport flight, a first day of school, or an exam.

\* \* \* \* \*